United States Patent [19]

Taylor

[11] 4,296,757
[45] Oct. 27, 1981

[54] RESPIRATORY MONITOR AND EXCESSIVE INTRATHORACIC OR ABDOMINAL PRESSURE INDICATOR

[76] Inventor: Thomas Taylor, 421 Randolph St., N.W., Washington, D.C. 20011

[21] Appl. No.: 139,686

[22] Filed: Apr. 14, 1980

[51] Int. Cl.³ .......................... A61B 5/08; A61B 5/10
[52] U.S. Cl. .................................. 128/721; 128/748; 128/782; 340/573
[58] Field of Search ............... 128/721, 722, 782, 748, 128/775, 690, 694; 340/573, 574

[56] References Cited

U.S. PATENT DOCUMENTS

| | | | |
|---|---|---|---|
| 3,097,639 | 7/1963 | Streimer | 128/721 |
| 3,268,845 | 8/1966 | Whitmore | 128/721 |
| 3,782,368 | 1/1974 | Reibold | 128/721 X |
| 3,882,847 | 5/1975 | Jacobs | 128/721 |

*Primary Examiner*—Kyle L. Howell
*Attorney, Agent, or Firm*—Armstrong, Nikaido, Marmelstein & Kubovcik

[57] ABSTRACT

The present invention is directed to a respiratory monitor for monitoring the respiration of a person. The respiratory monitor comprises a detector for detecting the expansion of the chest of the person and an alarm circuit coupled to the detector for producing an alarm signal if the detector does not detect expansion of the chest for a predetermined period of time. Further, a pressure monitor is provided for detecting excessive intrathoracic and/or abdominal pressure. A strap is provided for mounting the respiration detector and pressure monitor on the persons chest or abdomen, the strap including a cushion which compresses when the persons weight is placed thereon. The respiration detector and pressure monitor are mounted on the strap cushion such that when the person lies on his chest, the persons weight is absorbed by the cushion and the detector and monitor are not affected by the persons weight. The respiration detector and pressure monitor can be a normally open mechanical switches which are closed when the persons chest expands and when there is excessive pressure respectively. Further, the band or strap has an annular band having a protruding portion wherein the cushion is fixed to the protruding portion.

12 Claims, 5 Drawing Figures

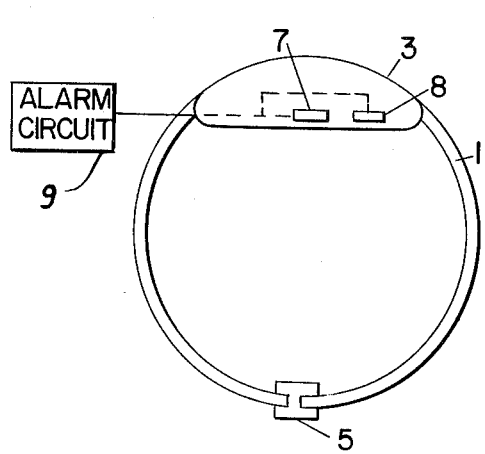
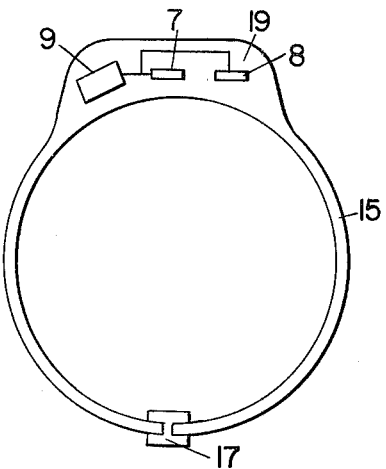
FIG. 1       FIG. 3
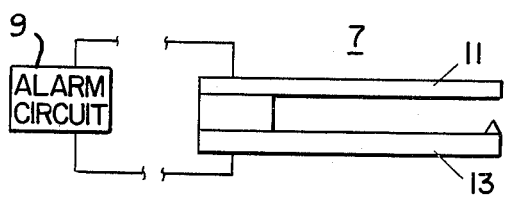
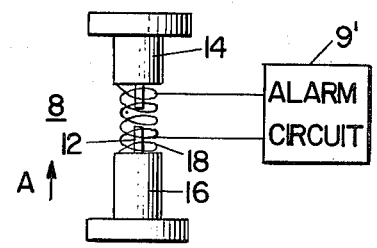
FIG. 2A       FIG. 2B
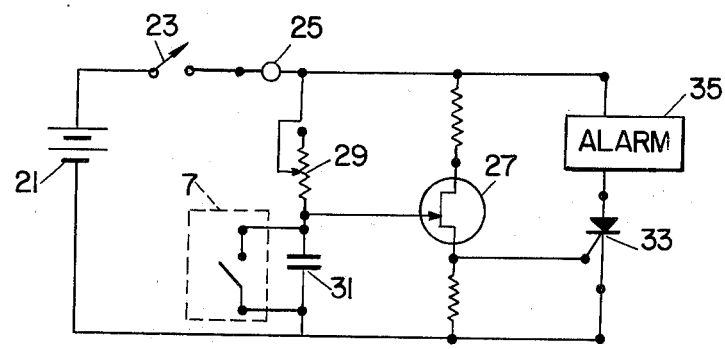
FIG. 4

RESPIRATORY MONITOR AND EXCESSIVE INTRATHORACIC OR ABDOMINAL PRESSURE INDICATOR

BACKGROUND OF THE INVENTION

1. Field of the Invention

This invention is directed to a respiratory monitor monitoring the respiration rate of a person and/or an excessive intrathoracic or abdominal pressure monitor and more particularly to a respiratory and pressure monitor which is not affected when the person using it rolls over. The device of the present invention is especially useful for the early detection of Sudden Infant Death Syndrome, thereby allowing time for action to be taken to prevent the death of an infant.

2. Description of the Prior Art

Sudden Infant Death Syndrome is the sudden and inexplicable death of an infant as a result of respiratory failure. Evidence has shown that at the onset of Sudden Infant Death Syndrome, there is an intense struggle by the infant to survive. High intrathroacic pressures appear to be involved. These pressures are substantially higher than those associated with a normal cough as is found in common colds. Also associated with Sudden Infant Death Syndrome is a cessation of respiration which ultimately results in death. Devices which monitor both respiration and excessive intrathoracic or abdominal pressure to provide an indication of the onset of Sudden Infant Death Syndrome have not been found in the prior art.

Prior art respiratory monitors are strapped to an individuals chest are known in the art. Two examples of these prior art devices are dislcosed in U.S. Pat. Nos. 3,097,639 and 3,268,845. Both of these prior art devices have a strap or band which fits around a persons chest and a variable resistance device connected between the ends of the strap. When the persons chest expands, the resistance of the resistance device is altered. This change in resistance is detected and is used to provide an indication of the individuals respiration rate.

Still another type of prior art respiration monitoring device is shown in U.S. Pat. No. 3,782,368 which discloses a piezoelectric device which is attached to a band or strap which is placed around a persons chest.

All of these prior art devices, however, have the disadvantage that the person whose respiration is being monitored must lie on their back or side when the detecting device is mounted on their chest. If the person rolls over under their chest, then the persons weight will be on the respiration detector and affect its operation. Certainly when a person is sleeping there is always the possibiity that he will roll over onto his chest and thus the effectiveness of the device, at its most critical time, that is when a person is sleeping, is greatly reduced. The lying of person on his chest would also affect the detection of intrathoracic or abdominal pressure.

SUMMARY OF THE INVENTION

It is the primary object of the present invention to provide a device for monitoring the respiration and/or intrathoracic pressure of a person especially an infant to detect the onset of Sudden Infant Death Syndrome or other respiratory ailment and thus to prevent its becoming fatal.

It is an object of the present invention to provide a respiratory monitor and/or an excessive intrathoracic or abdominal pressure monitor having a detector for detecting the expansion of a persons chest and/or excessive intrathoracic or abdominal pressure which includes means for absorbing the persons weight when he rolls over on his chest thereby eliminating the effect of a persons weight on the chest expansion detector or pressure monitor.

It is still another object of the present invention to provide a switch to open and close as a function of a persons respiration and to mount the switch in a respiration monitor within means for absorbing the persons weight when the person is lying on the respiration detector.

It is a further object of the present invention to provide a switch which closes in response to excessive intrathoracic or abdominal pressure and to mount the switch in a monitor within means for absorbing the persons weight when the person is lying on the pressure monitoring switch.

It is still another object of the present invention to provide a cushion, the respiration detector means and pressure monitor mounted therein wherein the cushion absorbs the weight of the person when the person lies on the respiration detector.

The present invention is directed to a respiratory monitor for monitoring the respiration of a person. The respiratory monitor comprises a detector for detecting the expansion of the chest of the person and an alarm circuit coupled to the detector for producing an alarm signal if the detector does not detect expansion of the chest for a predetermined period of time. The present invention further includes a pressure monitor for detecting excessive intrathoracic and/or abdominal pressure which occurs during Sudden Infant Death Syndrome. A strap is provided for mounting the respiration and pressure detectors on the persons chest, the strap including a cushion which compresses when the persons weight is placed thereon. The detectors are mounted on the strap cushion such that when the person lies on his chest, the persons weight is absorbed by the cushion and the detectors are not affected by the persons weight. The detectors can be a normally open mechanical switch which is closed when the persons chest expands or when there is excessive pressure. Further, the band or strap is an annular band having a protruding portion wherein the cushion is fixed to the protruding portion.

BRIEF DESCRIPTION OF THE DRAWINGS

FIG. 1 illustrates a respiration monitor of the present invention.

FIG. 2A illustrates a respiration detector used in the present invention.

FIG. 2B illustrates an excessive pressure monitor used in the present invention.

FIG. 3 illustrates an alternative embodiment of a respiration monitor of the present invention.

FIG. 4 illustrates an alarm circuit of the present invention.

DETAILED DESCRIPTION OF THE PREFERRED EMBODIMENTS

Referring to FIG. 1, the respiratory and pressure monitor of the present invention has a strap or band 1 of an elastic material which is attached to a compressible means 3 such as a pillow. The ends of the strap 1 are held together by fixing member 5 which may, for example, be a snap, buckle or Velcro fastener. The strap 1 is fixed around the chest of a person with the compressible member 3 against the persons chest. The compressible member 3, could, of course, be placed against other parts of the body such as side, abdomen, etc. as long as there is expansion at this point of the body as a result of breathing. A respiration detector 7 and excessive pressure monitor 8 are positioned within the compressible member 3 and the respiration detector 7 and excessive pressure monitor 8 are coupled to an alarm circuit 9.

Referring to FIG. 2A, detector 7 is a mechanical switch which comprises two conductive blades 11 and 13. The detector 7 is electrically connected to the alarm circuit 9. When blade member 13 is moved upward into contact with blade 11, an electrical circuit is completed with these members. The completion of the electrical circuit affects the operation of the alarm circuit 9.

In operation, the detector 7 is held close to a persons chest when the strap 1 is fastened around a persons chest. The member 13 is closest to the persons chest and referring to FIG. 2A, when the persons chest expands, the member 13 would move upward contacting member 11 and thereby completing the circuit. If a person wearing the respiratory monitor shown in FIG. 1 were to roll over then the persons weight would be on the detector 7 and member 11 would be pushed downward into contact with member 13 resulting in a false indication of chest expansion. However, the compressible member 3 is compressed by weight of the person using the device and thus absorbs this weight. The absorption of the weight by the compressible member 3 results in the member 11 not being brought into contact with member 13 to produce a false indication.

Referring to FIG. 2B, excessive pressure monitor 8 comprises two contacts 10 and 12 which are normally separated from one another. Contacts 10 and 12 are mounted on supports 14 and 16 respectively, the supports 14 and 16 being mounted within compressible member 3 and positioned with respect to the persons chest such that when there is excessive intrathoracic pressure, support 16 and thus, contact 12 moves toward support 14 and contact 10 in the direction of arrow A. When contact 10 makes contact with contact 12, an electrical circuit is completed which generates an alarm signal and alarm circuit 9'. Alarm 9' may be incorporated into alarm circuit 9 by connecting the contacts 10 and 12 to the alarm portion of alarm circuit 9. Spring 18 is positioned between supports 14 and 16 and biases these supports apart. Spring 18 is selected so that its biasing force is greater than the pressure which may be experienced during normal breathing and as a result of coughing due to common colds, etc. The biasing force of spring 18 is, however, not great enough to hold contacts 10 and 12 apart in response to excessive intrathoracic or abdominal pressure resulting from the occurrence of Sudden Infant Death Syndrome. Thus, upon the onset of Sudden Infant Death Syndrome, the excessive intrathoracic or abdominal pressure causes the closing of contacts 10 and 12 and thereby the generation of an alarm signal by alarm circuit 9'.

FIG. 3 illustrates an alternative embodiment of the present invention. In FIG. 3, strap or belt 15 is placed around a persons chest and fastened by a fastener 17. A compressible member 19 is integrally formed with the strap 15. A detector 7 is arranged within the compressible member 19 and detects the expansion of a persons chest. The alarm circuit 9 is also positioned within the compressible member 19.

The embodiment of FIG. 3 is a self contained or unitary respiratory monitor in that the alarm circuit is arranged within the compressible member. The pressure monitor 8 is also arranged within the compressible member. As can be seen, the compressible member is within a protrusion extending from the annular strap 15.

FIG. 4 illustrates one embodiment of an alarm circuit of the present invention. The circuit comprises a battery 21 connected in series with an on/off switch 23 and indicator lamp 25. Unijunction transistor 27 has its emitter connected to an RC circuit comprising variable resistor 29 and capacitor 31. The charging time of capacitor 31 can be controlled by means of variable resistor 29. When capacitor 31 is charged to a predetermined voltage, it will fire unijunction transistor 27 to a result in triggering of SCR 33. When SCR 33 is turned on, alarm circuit 35 will produce an alarm. Respiration detector 7 is connected across capacitor 31. The switch is a normally open switch and closes upon expansion of a persons chest. The charging rate of capacitor 31 is determined by means of resistor 29 so that if detector 7 is not closed within a predetermined period of time the charge on capacitor 31 turns on unijunction transistor 27 to thereby activate the alarm 35. Resistor 29 is set so that if the person is breathing at a normal rate, switch 7 will be closed before the voltage across capacitor 31 turns on the unijunction transistor 27. However, if breathing is slow or if a person stops breathing, switch 7 will not be closed, capacitor 31 will turn on transistor 27 and alarm 35 will thereby be activated.

The excessive pressure monitor shown in FIG. 2B can also be coupled to alarm 35 such that the closing of contacts 10 and 12 will activate the alarm 35.

The present invention may be embodied in other specific forms without departing from the spirit or essential characteristics thereof. The presently disclosed embodiments are, therefore, to be considered in all respects as illustrative and not restrictive, the scope of the invention being indicated by the appended claims, rather than the foregoing description, and all changes which come within the meaning and range of equivalency of the claims are, therefore, to be embraced therein.

What is claimed is:

1. A respiratory monitor for monitoring the respiration of a person said respiratory monitor comprising:
   (a) detector means for detecting the expansion of the chest of the person;
   (b) alarm circuit means coupled to said detector means for producing an alarm signal if said detector means does not detect expansion of the chest for a predetermined period of time; and
   (c) strap means for mounting said detector means on the persons chest said strap means including compression means for compressing when the persons weight is placed thereon wherein said detector means are mounted on said strap means such that when the person lies on his chest the persons weight is absorbed by said compression means whereby said detector means is not affected by the position of the person.

2. A respiratory monitor as set forth in claim 1, further including a pressure monitoring means for monitoring excessive intrathoracic or abdominal pressure, said pressure monitoring means being mounted on said strap means and said pressure monitoring means being coupled to said alarm circuit means wherein said alarm circuit means produces an alarm when said pressure monitoring means detects an intrathoracic or abdominal pressure greater than a predetermined pressure.

3. A respiratory monitor as set forth in claims 1 or 2, wherein said compression means is a cushion and wherein said strap means is elastic.

4. A respiratory monitor as set forth in claim 3, wherein said detector means is mounted within said cushion.

5. A respiratory monitor as set forth in any of claims 1 or 2, wherein said detector means is a switch means.

6. A respiratory monitor as set forth in claim 2, wherein said pressure monitoring means is a switch means.

7. A respiratory monitor as set forth in claim 5, wherein said switch means is normally open and said switch means is closed when the persons chest expands a predetermined amount.

8. A device for mounting a respiration detector and pressure monitor on a persons chest, said device comprising:

(a) band means for wrapping around the persons chest; and (b) weight absorption means, fixed to said band means, having a first portion which is compressed by the weight of the person when the weight of the person is on the weight absorption means and a second portion which is not compressed by the persons weight wherein said respiration detector and pressure monitor are mounted in said second portion.

9. A device as set forth in claim 8, wherein said respiration detector means is a mechanical switch.

10. A device as set forth in claim 8, wherein said pressure monitor is a mechanical switch.

11. A device as set forth in any of claims 8-10, wherein said weight absorption means is a cushion.

12. A device as set forth in claim 11, wherein said band means is an annular band having a protruding portion and wherein said weight absorption means is fixed to said protruding portion.

* * * * *

UNITED STATES PATENT AND TRADEMARK OFFICE
CERTIFICATE OF CORRECTION

PATENT NO. : 4,296,757
DATED : October 27, 1981
INVENTOR(S) : Thomas Taylor

It is certified that error appears in the above—identified patent and that said Letters Patent is hereby corrected as shown below:

In the drawings Figure 2B should appear as shown below.

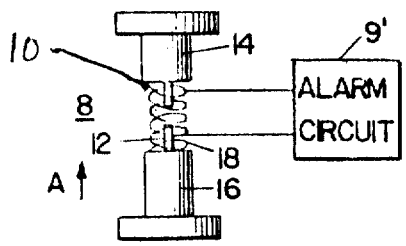

*FIG. 2B*

Signed and Sealed this

Twenty-third Day of February 1982

[SEAL]

Attest:

Attesting Officer

GERALD J. MOSSINGHOFF
Commissioner of Patents and Trademarks